(12) United States Patent
Horian

(10) Patent No.: US 6,289,907 B1
(45) Date of Patent: Sep. 18, 2001

(54) DEVICE AND METHOD FOR CLEANING CONTACT LENSES

(76) Inventor: Richard C. Horian, 11952 Montana Ave., #102, Los Angeles, CA (US) 90049

( * ) Notice: Subject to any disclaimer, the term of this patent is extended or adjusted under 35 U.S.C. 154(b) by 0 days.

(21) Appl. No.: 09/244,352

(22) Filed: Feb. 4, 1999

(51) Int. Cl.[7] .................................................. B08B 3/02
(52) U.S. Cl. ...................... 134/149; 134/147; 134/153; 134/140; 134/901
(58) Field of Search .................................. 134/147, 153, 134/200, 140, 141, 149, 301

(56) References Cited

U.S. PATENT DOCUMENTS

| | | | |
|---|---|---|---|
| D. 312,086 | 11/1990 | Emmett | D16/124 |
| D. 328,134 | 7/1992 | Yang | D24/218 |
| D. 341,615 | 11/1993 | Ifejika | D16/124 |
| D. 354,070 | 1/1995 | Chen | D16/331 |
| 3,623,492 | 11/1971 | Frantz et al. | 134/143 |
| 3,822,780 | 7/1974 | Ulmer et al. | 206/5.1 |
| 3,966,076 | 6/1976 | Kroger et al. | 220/20 |
| 3,991,779 * | 11/1976 | Saurenman . | |
| 3,997,049 | 12/1976 | Sherman | 206/5.1 |
| 4,011,941 | 3/1977 | Parsons | 206/5.1 |
| 4,396,583 | 8/1983 | LeBoeuf | 422/301 |
| 4,503,873 * | 3/1985 | Edebo et al. . | |
| 4,582,076 * | 4/1986 | Prat | 134/901 |
| 4,776,360 | 10/1988 | Ching Shih | 134/140 |
| 4,807,750 | 2/1989 | Ryder et al. | 206/5.1 |
| 4,814,109 | 3/1989 | Wittpenn, Jr. et al. | 252/547 |
| 4,816,232 * | 3/1989 | Barrau et al. | 134/901 |
| 4,907,613 * | 3/1990 | Litzaw | 134/901 |
| 4,957,128 | 9/1990 | Chen | 134/118 |
| 5,117,849 * | 6/1992 | Zimmerli | 134/901 |
| 5,181,604 * | 1/1993 | Ohta et al. | 134/901 |
| 5,186,317 | 2/1993 | Ryder et al. | 206/5.1 |
| 5,232,003 | 8/1993 | Wei et al. | 134/158 |
| 5,234,010 | 8/1993 | Grondin | 134/140 |
| 5,388,686 | 2/1995 | Kanner et al. | 206/5.1 |
| 5,690,211 | 11/1997 | Jao | 206/5.1 |

FOREIGN PATENT DOCUMENTS 4-13114 * 1/1992 (JP) ..................................... 134/901

OTHER PUBLICATIONS

EPO 354,876 134/901, Feb. 1990.*
WIPO 81/01884 134/901, Feb. 1990.*

* cited by examiner

Primary Examiner—Frankie L. Stinson
(74) Attorney, Agent, or Firm—Lyon & Lyon LLP

(57) ABSTRACT

A device for cleaning soft contact lenses includes a cage having two cavities to loosely receive soft contact lenses therein. The cavities are defined by spaced ribs and provide surfaces approximating the surfaces of the lenses to be contained therein. The cage is positionable within a container which is fluid tight and can be associated with a rotary drive. The drive is oriented to rotate the container in a horizontal axis. The container includes an appropriate fill line allowing filling of one-half of the internal volume of the container with multipurpose liquid or cleaning solution. The rims of the lenses contained within the cage are arranged with the planes of such lenses substantially parallel to the axis of rotation and displaced from that axis to accommodate lifting the lenses repeatedly out of the body of liquid and then fully immersing them. A method for cleaning contact lenses includes loosely containing the lens so that it may move about the cage, repeatedly moving the lens fully into and out of a body of liquid through rotation in a substantially horizontal axis. The lenses are rotated slowly at three to ten revolutions per minute.

12 Claims, 6 Drawing Sheets

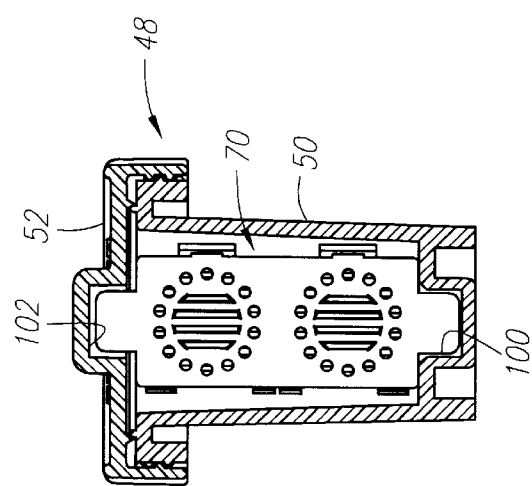
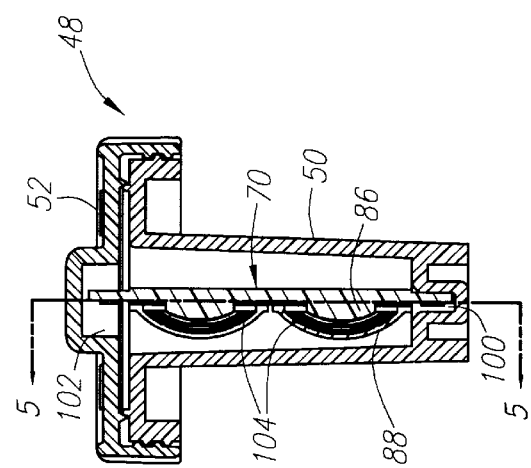
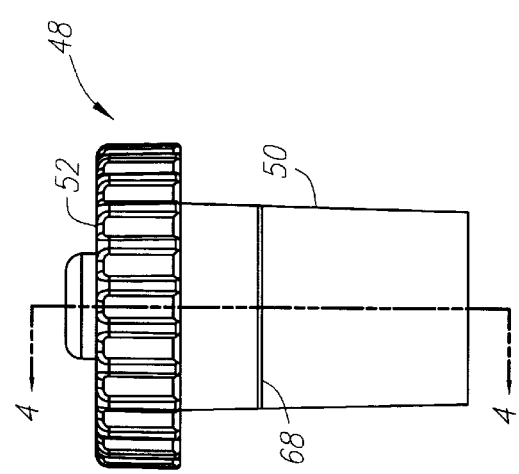

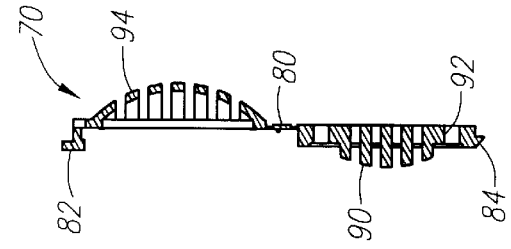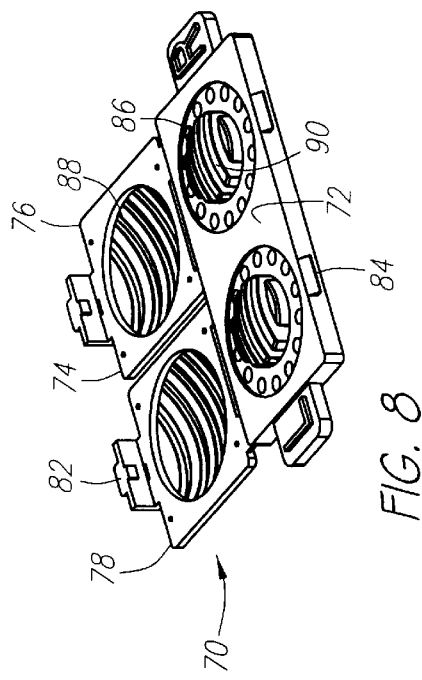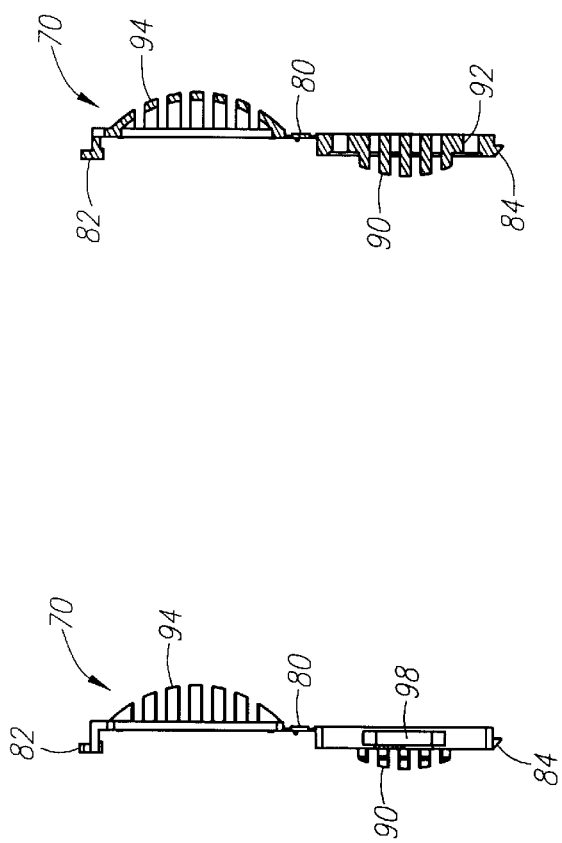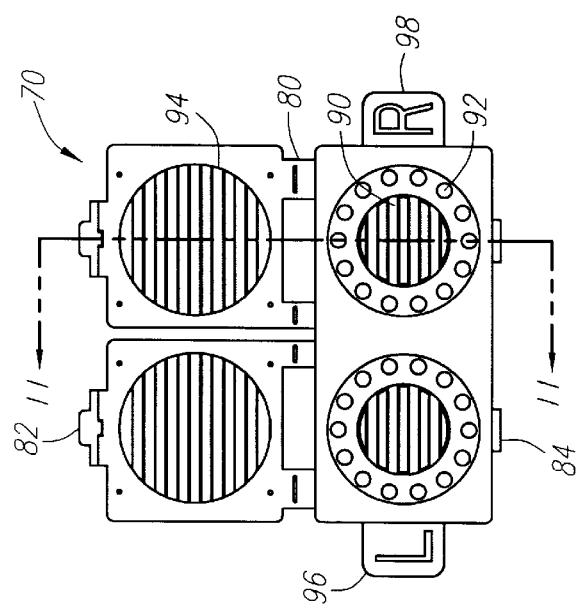

DEVICE AND METHOD FOR CLEANING CONTACT LENSES

BACKGROUND OF THE INVENTION

The field of the present invention is cleaning systems for soft contact lenses.

There have been many devices considered over the years to automatically clean soft contact lenses. These devices have varied in their levels of effectiveness, safety to the lens and wearer, cost of materials required and cost of the device itself. The disadvantages in effectiveness and practicality of such devices have left the preferred method of cleaning lenses recommended by most manufacturers to be that of manual cleaning by the wearer.

The current, most widely recommended method of cleaning is for the wearer to wash their hands, remove the contact lenses, position the lenses in the cupped palm or between two fingers and physically rub the lenses with a finger in conjunction with applying cleaning fluid designed for the purpose. In recent years, this task has been made a bit simpler by the development of "all-in-one" contact lens fluid formulations. These formulations allow a single fluid to be used to store, rinse, disinfect and clean the contact lenses. However, due to the relative levels of effectiveness and practicality, no simple automated machine has been found to be in widespread use. Manual cleaning as described above remains as the predominant method of choice.

Manual cleaning has certain disadvantages. It is a delicate operation requiring great dexterity and subtlety of touch not suited to many people. Lenses can easily be dropped and lost or torn during this operation. To thoroughly clean the lenses, the operation can be time consuming. As the process is typically performed before retiring and/or after rising, such procedures can be inconvenient. Finally, wearers are typically faced with the problem of attempting to manually clean such delicate lenses without clear vision.

In addition to the foregoing obvious difficulties with manual cleaning, there are ergonomic limitations on the process. Rubbing the lens between fingers or with a finger placed in the palm can simply rub debris and substances into the lens or across the face of the lens. The action is one of scrubbing with the debris between the finger and the lens. There is no concurrent rinsing action to expel rather than rub in the debris and unwanted substances. Further, fingers are never truly clean and can simply add debris and substances to the lens itself.

SUMMARY OF THE INVENTION

The present invention is directed to a system for cleaning soft contact lenses. The system provides for a lens to be repeatedly moved into and out of a body of liquid and provides for the lens to move about the loosely constraining enclosure to enhance the cleansing action.

In a first separate aspect of the present invention, a device for cleaning soft contact lenses includes a cage having one or more cavities sized to receive a soft contact lens in each cavity with clearance about the lens and with interstices for fluid flow therethrough. A rotary drive is coupled to the cage which drives the cage about a substantially horizontal axis with a lens contained therein being displaced from the axis. The device may additionally include a fluid type container to receive the cage and to be driven in turn by the rotary drive. By filling the container partway full, a lens positioned within the device may be repeatedly removed into and out of cleaning liquid.

In a second separate aspect of the present invention, a device for cleaning soft contact lenses includes a cage for receiving such lenses, a liquid-tight container and a rotary drive. The drive is able to rotate the container about a horizontal axis. The cage may be contained within the container and includes tabs at either end. The container receives the tabs in the sockets with one of the sockets preventing relative rotation of the cage and the container.

In a third separate aspect of the present invention, a device for cleaning soft contact lenses includes a cage for loosely receiving such lenses and a rotary drive to rotate the lenses about a substantially horizontal axis. The lenses are displaced from the axis of rotation. The cage includes two cavities with each cavity having a convex surface and a concave surface which are in mating orientation and displaced from one another to each receive a lens. Spaced ribs may be additionally incorporated with this aspect of the invention to define the convex and concave surfaces. The ribs may be arranged parallel to the axis of rotation and provide fluid flow through the cage and reduced forces imposed by surface tension which would otherwise retain a lens from significant movement within the cage.

In a fourth separate aspect of the present invention, a cage for containing soft contact lenses in a device for cleaning soft contact lenses includes two cavities sized to receive the contact lenses with clearance and interstices for fluid flow through the cavities. The cage has two sections joined by a living hinge and held in place by a clasp to provide the cavities with convex and concave surfaces which are in mating orientation and displaced apart to receive the lenses. A rotary drive provides an axis of rotation which is displaced from the concave side of the lenses to provide the capability of repeatedly moving the lenses fully into and out of a body of liquid.

In a fifth separate aspect of the present invention, a method for cleaning soft contact lenses includes loosely containing the lenses and repeatedly moving the lenses fully into and out of a body of liquid. The lenses are oriented such that they can move into and out of a body of liquid with the liquid able to wash over or drain from the lenses across the surfaces thereof.

In a sixth separate aspect of the present invention, a method for cleaning soft contact lenses includes loosely containing the lenses and rotatably mounting the lenses about an axis which is horizontal and displaced from the concave side thereof to again provide the ability to move the lenses repeatedly into and out of a body of liquid.

A seventh separate aspect of the present invention includes the combination of any of the foregoing aspects.

Thus, an improved system of cleaning soft contact lenses is disclosed. Other and further objects and advantages will appear hereinafter.

BRIEF DESCRIPTION OF THE DRAWINGS

FIG. 3 is a side view of a fluid-tight container.

FIG. 4 is a cross-sectional view taken along line 4—4 of FIG. 3.

FIG. 5 is a cross-sectional view taken along line 5—5 of FIG. 4.

FIG. 8 is a perspective view of a lens cage.

FIG. 9 is a plan view of the lens cage of FIG. 8.

FIG. 10 is an end view of the lens cage of FIG. 8.

FIG. 11 is a cross-sectional view of the lens cage taken along line 11—11 of FIG. 9.

DETAILED DESCRIPTION OF THE PREFERRED EMBODIMENT

Figure 1:
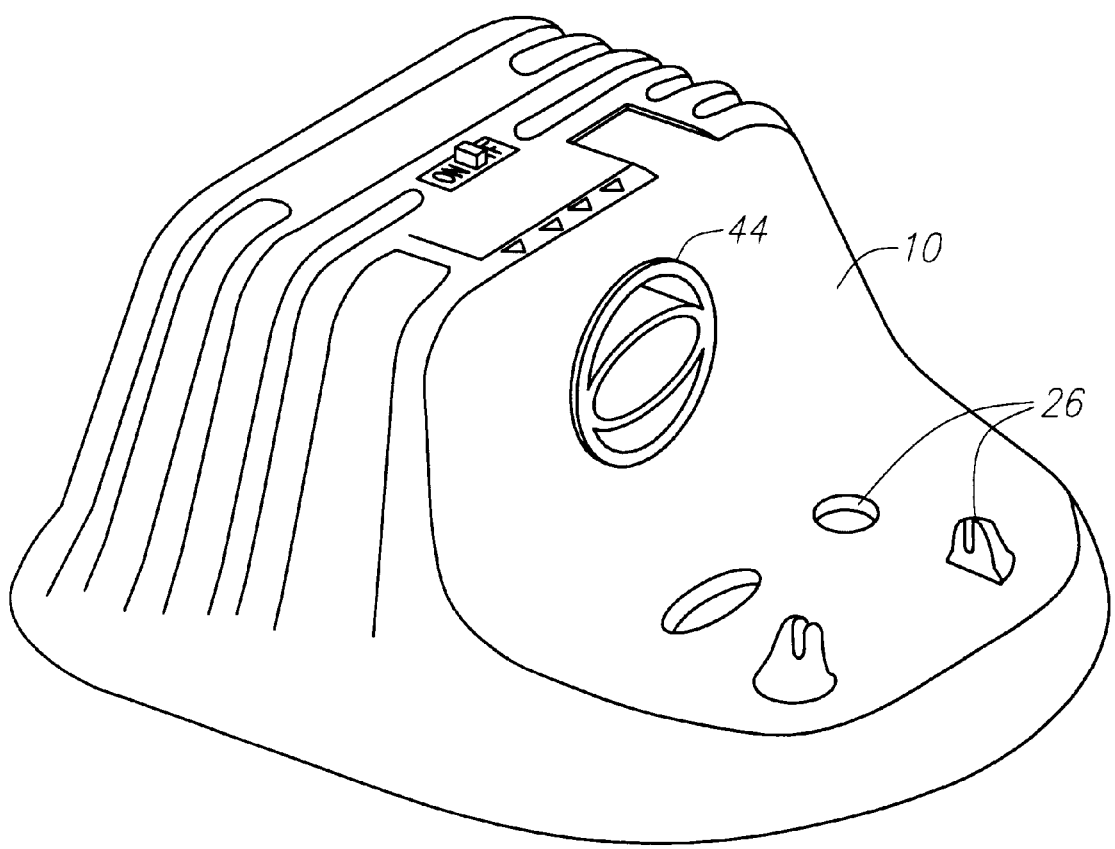
FIG. 1 is a perspective view of a device for cleaning soft contact lenses.
Figure 2:
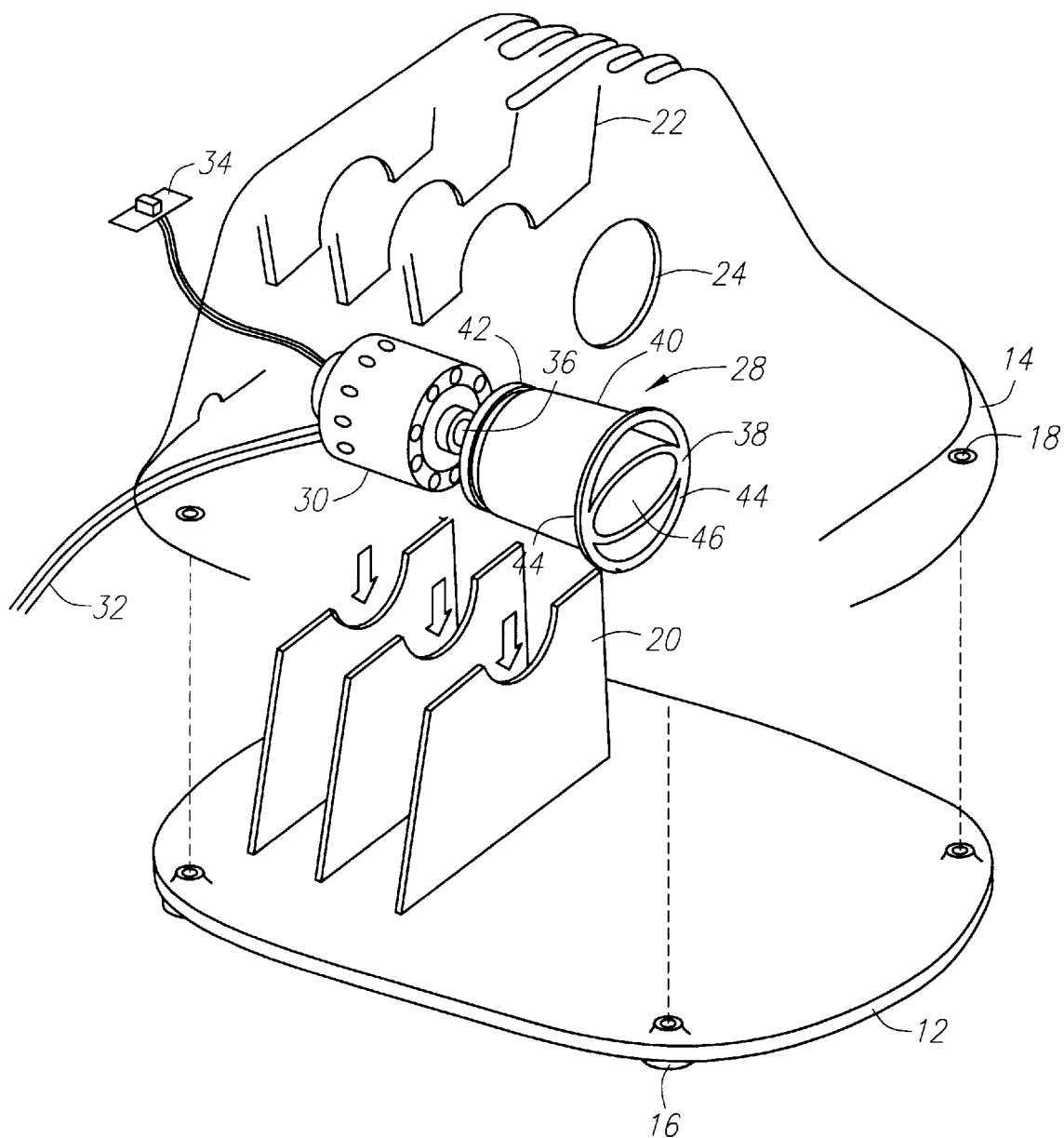
FIG. 2 is a partially exploded and broken away perspective view of the device of FIG. 1.

Turning in detail to the drawings, a device for cleaning soft contact lenses is disclosed. The fully assembled device is illustrated in FIG. 1 as including a covering housing 10. The housing 10 includes a base 12 and a cover 14 as seen in FIG. 2. Fasteners complete the closure by extending through the feet 16 of the base 12 to engage flanges having holes 18 to receive and hold the fasteners. Mounting plates 20 integrally formed with the base 12 and mounting plates 22 integrally formed with the cover 14 come together with assembly of the base 12 and cover 14 to define circular journals for receiving the operative components of the device. An access hole 24 is aligned with the circular journals and opens through the cover 14. Sockets 26 of various configuration are provided on the face of the housing 10 to receive the container, the lens holder, multipurpose or cleaning solutions, and the like as may be most convenient for use of the device.

A rotary drive 28 is held within the circular journals of the mounting plates 20 and 22. The rotary drive 28 includes a motor 30 held fixed within the rear two circular journals defined by the mounting plates 20 and 22. A power cord 32 and a switch 34 extend from the interior of the housing 10. The switch may be conventionally mounted to the cover 14. The motor 30 may include an integral gear box or one separately provided to reduce the speed of rotation of the output from the motor 30. The output is contemplated to be three to ten revolutions per minute with appropriate speed reductions. A shaft 36 from the motor assembly 30 extends to a rotatably mounted rotary mount 38. The rotary mount 38 includes an outer shell 40 of circular cross section. The shell 40 may either be cylindrical or conical. A groove 42 about the shell 40 is received in the forwardmost circular journals of the mounting plates 20 and 22. The access hole 24 mounts the other end of the shell 40. A lip 44 on the shell 40 additionally assists in the location of the shell 40 by preventing the entire assembly from being pushed further into the housing 10.

The shell 40 includes an oblong cavity 46. The oblong cavity 46 is arranged in this embodiment such that the center of the cross-sectional area of the oblong cavity 46 is coincident with the axis of rotation of the rotary drive 28. The cavity, as is also true of the axis, extends substantially horizontally in the device assuming conventional placement of the device on the feet 16 of the base 12.

Figure 6:
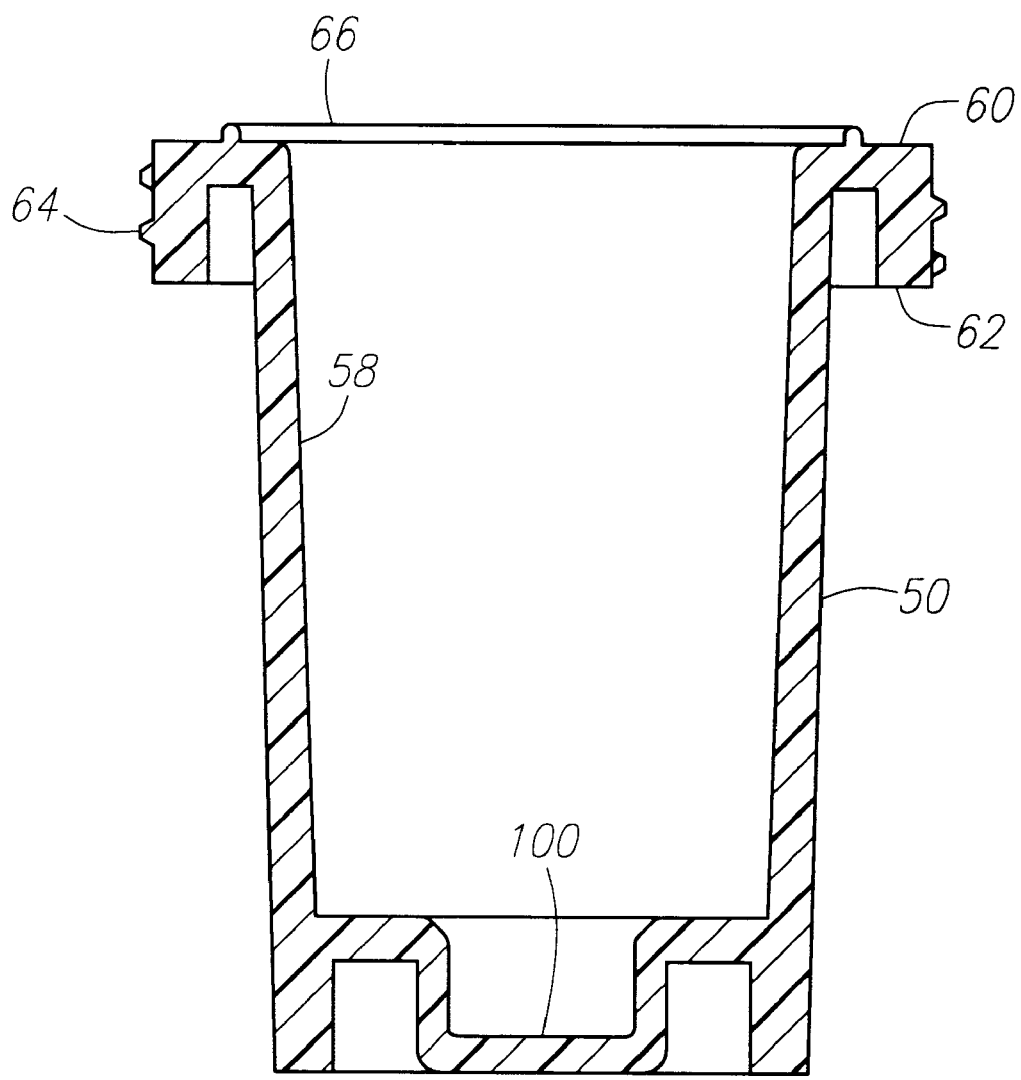
FIG. 6 is a cross-sectional view of the container jar viewed in the same direction as in FIG. 5.
Figure 7:
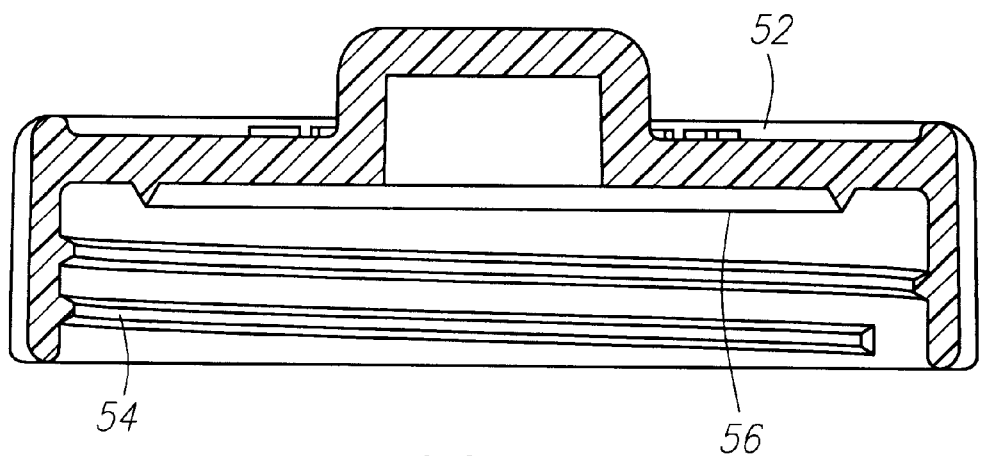
FIG. 7 is a cross-sectional view of the liquid-tight lid of the container viewed in the same direction as FIG. 5.

FIGS. 3, 4 and 5 show an assembled fluid-tight container, generally designated 48. The container 48 is shown to include a jar 50 and a fluid-tight lid 52. The jar 50 is illustrated in cross section in FIG. 6 while the lid 52 is illustrated in cross section in FIG. 7. The lid 52 is substantially circular in overall construction and includes internal threads 54 and an integral seal 56. The jar 50 includes a central cavity 58 which is oblong in cross section. A flange 60 extends outwardly from an open end of the cavity 58. A depending cylinder 62 includes threads 64 to receive the threads 54 of the fluid-tight lid 52. The jar 50 also includes an integral seal 66 as can be seen in FIG. 6. The jar 50 and the lid 52 can be tightly threaded together to provide a fluid-tight seal. A fill line 68 divides the interior volume of the fluid-tight container 48 at one-half.

A lens cage, generally designated 70, is shown in position with the fluid-tight container 48 in FIGS. 4 and 5 and is separately illustrated in FIGS. 8 through 11. The cage 70 includes two mating sections, the convex section 72 and the concave section 74. The concave section 74 is divided into two cavity elements 76 and 78 in order that one lens may be manipulated at a time. The sections 72 and 74 are coupled together by thin portions of the unitary structure often referred to as living hinges 80. The attachment of the sections 72 and 74 at the living hinges 80 is along one side of each of the sections. A clasp assembly is provided on the other side of each of the sections 72 and 74. A resilient hook 82 is on one of the elements while a bar 84 is located to receive the hook 82 with regard to each of the two clasps associated with the cavity elements 76 and 78, respectively.

The cage 70 includes two cavities 104 which are defined by two convex surfaces 86 and two concave surfaces 88 as illustrated in FIG. 4. The convex surfaces 86 located on the convex section 72 include convex, spaced ribs 90. Holes 92 are arranged about the spaced ribs 90. The spaces between the ribs 90 and the holes 92 define interstices which allow the fluid within the fluid-tight container 48 to flow quite freely through the convex surface 86.

The concave surfaces 88 also include spaced ribs 94. These ribs 94 are concave. The spacing between the ribs 94 again allows free flow of fluid therethrough.

Through the freedom of the living hinges 80, the two mating sections 72 and 74 can be mutually overlaid with the clasp assembly holding the components in place. In this configuration, the convex, spaced ribs 90 and the concave, spaced ribs 94 forming the convex surfaces 86 and the concave surfaces 88 achieve a mating orientation but are displaced apart for receipt of contact lenses within the cavities defined. With a contact lens in place, the cavities of the cage 70 are intended to have a clearance about the lens of 0.025 inches to 0.065 inches. With the cage 70 in the closed configuration, the two cavities for receiving contact lenses are arranged laterally adjacent with the convex, spaced ribs 90 and the concave, spaced ribs 94 extending longitudinally in the same direction as the lateral placement of these adjacent cavities.

Tabs 96 and 98, conveniently indicating left and right, are also aligned to either end of the same configuration. The tabs are shown to be aligned with the body of the convex section 72 such that the convex, spaced ribs 90 are displaced outwardly from the tabs 96 and 98. Thus, lenses arranged in the cavities of the cage 70 have the concave sides thereof facing and displaced from an axis through the tabs 96 and 98 such that the rims of the contact lenses define planes which are substantially parallel to this same axis when the lenses are symmetrically positioned within the cavities.

In addition to indicating left and right lenses and providing convenient handles for holding the cage 70, the tabs 96 and 98 are employed to locate and to retain the cage 70 within the fluid-tight container 48. A socket 100 is located in the bottom of the cavity 58. This socket 100 is asymmetrical about an axis extending through the socket such that whichever tab 96 and 98 is positioned in the socket 100 becomes non-rotatable relative to the cavity 58. A second socket 102 is located in the center of the fluid-tight lid 52. This socket is symmetrical about the same axis and receives one or the other of the tabs 96 and 98 such that the tab is rotatable within the socket 102. By separately configuring the sockets 100 and 102, the cage 70 is retained from rotating within the fluid-tight container 48 but the fluid-tight lid 52 can be threaded onto the jar 50 with rotation relative to the cage 70.

To complete the assembly, soft contact lenses are placed in the concave surfaces 88 within the cage 70. The convex surfaces 86 are then brought into mating orientation such that the hooks 82 and bars 84 close the clasps. One or the other of the tabs 96 and 98 is inserted into the socket 100 within the cavity 58. The fluid tight lid 52 is then placed on the jar 50, making sure that the other tab 96 and 98 is arranged in the socket 102. Multipurpose solution or cleaning solution is then introduced into the cavity 58 to fill line 68. The fluid-tight lid 52 is then placed on the jar 50, insuring that the other tab 96 and 98 is positioned in the socket 102. The lid 52 is then tightened on the jar 50 to achieve a fluid-tight condition for the container 48.

The orientation of the cage 70 in the fluid-tight container 48 with the tabs 96 and 98 laterally offset from the convex surface 86 aligns the central axis of the container 48 parallel to the spaced ribs 90 and 94 and displaced from the concave surfaces of lenses placed within the cage 70 and with the planes defined by the rims of the lenses being substantially parallel to this axis of rotation. The fluid-tight container 48 may then be placed in the rotary mounting 38 of the rotary drive 28. The container 48 is sized to mate with the rotary mounting 38 in interference fit. With the container 48 half filled with fluid and arranged about a substantially horizontal axis, the displaced lenses, when rotated, move fully into and fully out of the body of liquid within the container 48. Given the orientation of the cage 70 with the horizontal axis being displaced from the concave side, lenses placed within the cavities avoid having an upwardly facing concavity when the lens is out of the fluid and also avoid having a downward facing concavity when the lens is in the fluid. This avoids retention of fluid on the lens or retention of air on the lens.

With the configuration as above described, lenses can be cleaned by this device for cleaning contact lenses over a period of a few hours. Conveniently, lenses are placed in the device at night before retiring. The next morning, the lenses are clean and ready to be appropriately rinsed and worn. The lenses are placed in the loosely containing cavities of the cage 70 with the convex surfaces 86 and 88 approximating the curvature of the adjacent lens surface. The rotary drive 28 is activated and, with the appropriate level of fluid in the container, the lenses begin to rotate from fully out of the solution to fully immersed in the solution and then out again. This rotation into and out of the solution allows the hydrophilic lens to become fully gorged with liquid and then begin to disgorge the liquid. The movement as the lens enters the body of fluid or leaves the body of fluid allows for convenient flow substantially parallel to the surface of the lens to sweep off debris and foreign substances. The slow movement of the cage at three to ten revolutions per minute allows the lens to move somewhat within the cavities in the cage 70. The light contact of the curved surfaces defining the cavities further operates to assist in the cleaning process. The ribs, being parallel to the axis of rotation, can be disruptive of the relative fluid flow through the cavities and provide edges which can lightly scrape across the ever-moving lenses. The spaces between ribs facilitates the release of the lenses from the surfaces defining the cavities of the cage 70. Thus, a number of cleaning actions take place with the present device.

Thus, a soft contact lens cleaning system has been disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. The device for cleaning soft contact lenses, the container including a jar and a liquid tight lid.

2. A device for cleaning soft contact lenses, comprising
   a cage including at least one cavity sized to receive a soft contact lens with clearance about the soft contact lens and including interstices for fluid flow through the at least one cavity;
   a rotary drive operatively coupled to the cage with the axis of the rotary drive being substantially horizontal, the cage being oriented with the substantially horizontal axis of the rotary drive being substantially parallel to the plane of the rim of a soft contact lens within the cage and displaced from the plane;
   a fluid tight container receiving the cage, the container including a jar and a liquid tight lid, the jar having a first socket and the lid having a second socket opposed to the first socket with the jar mated with the liquid tight lid, one of the first and second sockets being asymmetrical about an axis extending through the first and second sockets and the other of the first and second sockets being symmetrical about the axis extending through the first and second sockets, the cage further including first and second tabs each positionable within the first and second sockets, each tab being rotatable within the symmetrical socket and non-rotatable within the asymmetrical socket.

3. A device for cleaning soft contact lenses, comprising
   a cage including at least one cavity sized to receive a soft contact lens with clearance about the soft contact lens and including interstices for fluid flow through the at least one cavity;
   a rotary drive operatively coupled to the cage with the axis of the rotary drive being substantially horizontal, the cage being oriented with the substantially horizontal axis of the rotary drive being substantially parallel to the plane of the rim of a soft contact lens within the cage and displaced from the plane;
   a fluid tight container receiving the cage, the rotary drive receiving the fluid tight container and being directly coupled therewith, the cage being fixable in the fluid tight container.

4. The device for cleaning soft contact lenses of claim 3, the jar being oblong in cross section.

5. The device for cleaning soft contact lenses of claim 3, the jar having a fill line at one-half the volume of the interior of the container with the jar mated with the liquid tight lid.

6. The device for cleaning soft contact lenses of claim 3, the rotary drive including a cavity to receive the fluid tight container in interference fit.

7. The device for cleaning soft contact lenses of claim 6, the cage including two of the at least one cavity laterally adjacent and extending along the substantially horizontal axis of the rotary drive.

8. The device for cleaning contact lenses of claim 3, the rotary drive including a motor.

9. The device for cleaning contact lenses of claim 3, the horizontal axis of the rotary drive being displaced from the plane on the concave side of the lens.

10. A device for cleaning contact lenses, comprising
   a cage including two cavities sized to receive a soft contact lens each with clearance about the soft contact lens and including interstices for fluid flow through the cavities, the cavities each having a convex surface and a concave surface in mating orientation and displaced apart from one another;

a fluid tight container receiving the cage and including a jar and a liquid tight lid, the jar having a fill line at one-half the volume of the interior of the container with the jar mated with the liquid tight lid, the jar having a first socket and the lid having a second socket opposed to the first socket with the jar mated with the liquid tight lid, one of the first and second sockets being asymmetrical about an axis extending through the first and second sockets and the other of the first and second sockets being symmetrical about the axis extending through the first and second sockets, the cage further including first and second tabs each positionable within the first and second sockets, each tab being rotatable within the symmetrical socket and non-rotatable within the asymmetrical socket;

a rotary drive operatively coupled to the fluid tight container with the axis of the rotary drive being substantially horizontal, the cage in the fluid tight container being oriented with the substantially horizontal axis of the rotary drive being substantially parallel to the plane of the rim of a soft contact lens within the cage and displaced from the plane on the concave side of the lens, the two cavities being laterally adjacent and extending along the substantially horizontal axis of the rotary drive.

11. The device for cleaning soft contact lenses of claim 10, the cage further including spaced ribs defining the convex surface and the concave surface, the ribs extending at parallel to the substantially horizontal axis of the rotary drive.

12. The device for cleaning soft contact lenses of claim 10, the cage having two mating sections with a living hinge therebetween on one side of each of the two mating sections and a clasp therebetween on an opposite side of each of the two mating sections, the convex surfaces being on one of the two mating sections and the concave surfaces being on the other of the two mating sections.

* * * * *

UNITED STATES PATENT AND TRADEMARK OFFICE
CERTIFICATE OF CORRECTION

PATENT NO.    : 6,289,907 B1
DATED         : September 18, 2001
INVENTOR(S)   : Richard C. Horian It is certified that error appears in the above-identified patent and that said Letters Patent is hereby corrected as shown below:

Please rewrite claim 1 as follows:
    1.     The device for cleaning soft contact lenses of claim 3, the container including a jar and a liquid tight lid.

Signed and Sealed this

Twenty-third Day of April, 2002

Attest:

JAMES E. ROGAN
Attesting Officer      *Director of the United States Patent and Trademark Office*